(12) United States Patent
Suri et al.

(10) Patent No.: US 8,450,491 B2
(45) Date of Patent: May 28, 2013

(54) METHOD FOR THE PREPARATION OF MONTELUKAST ACID AND SODIUM SALT THEREOF IN AMORPHOUS FORM

(75) Inventors: Sanjay Suri, New Delhi (IN); Jujhar Singh, New Delhi (IN); Gurdeep Singh Sarin, New Delhi (IN); Madan Pal Tanwar, New Delhi (IN); Manu Mahendru, New Delhi (IN)

(73) Assignee: Morepen Laboratories Limited, New Delhi (IN)

( * ) Notice: Subject to any disclaimer, the term of this patent is extended or adjusted under 35 U.S.C. 154(b) by 1558 days.

(21) Appl. No.: 10/576,971

(22) PCT Filed: Jun. 6, 2003

(86) PCT No.: PCT/IN03/00214
§ 371 (c)(1),
(2), (4) Date: Apr. 25, 2006

(87) PCT Pub. No.: WO2004/108679
PCT Pub. Date: Dec. 16, 2004

(65) Prior Publication Data
US 2007/0082925 A1    Apr. 12, 2007

(51) Int. Cl.
*C07D 215/04*    (2006.01)
*A61K 31/47*    (2006.01)

(52) U.S. Cl.
USPC .......................................... 546/181; 514/311

(58) Field of Classification Search
USPC .......................................... 514/311; 546/181
See application file for complete search history.

(56) References Cited

U.S. PATENT DOCUMENTS

| 5,565,473 A | 10/1996 | Belley et al. |
| 5,614,632 A | 3/1997 | Bhupathy et al. |
| 6,320,052 B1 * | 11/2001 | Bhupathy et al. ............. 546/174 |

FOREIGN PATENT DOCUMENTS

| EP | 0 480 717 A1 | | 4/1992 |
| WO | WO 03/066598 | * | 8/2003 |

OTHER PUBLICATIONS

Harwood and Moody in Experimental Organic Chemistry: Principles and Practice, Blackwell Scientific Publications 1989, pp. 127-138.*

* cited by examiner

*Primary Examiner* — John Mabry
(74) *Attorney, Agent, or Firm* — Reed Smith LLP; Nanda P. B. A. Kumar

(57) ABSTRACT

A method for the preparation of montelukast acid sodium salt thereof in amorphous form has been described. The method comprises of following steps: (a) generating the dilithium dianion of 1-(mercaptomethyl)cyclopropane acetic acid, by reacting with alkyl lithium, (b) coupling the said dianion with wet mesylate to get montelukast acid in crude form, (c) obtaining DCHA salt in crude form by adding dicyclohexylamine (DCHA) to crude acid obtained in the above step (b), (d) purifying and converting the said DCHA salt in crude form, to montelukast acid in pure form, and (e) reacting the pure montelukast acid in a polar protic solvent with a source of sodium ion followed by evaporating the solvent and triturating of the residue with non-polar water immiscible solvent.

5 Claims, 1 Drawing Sheet

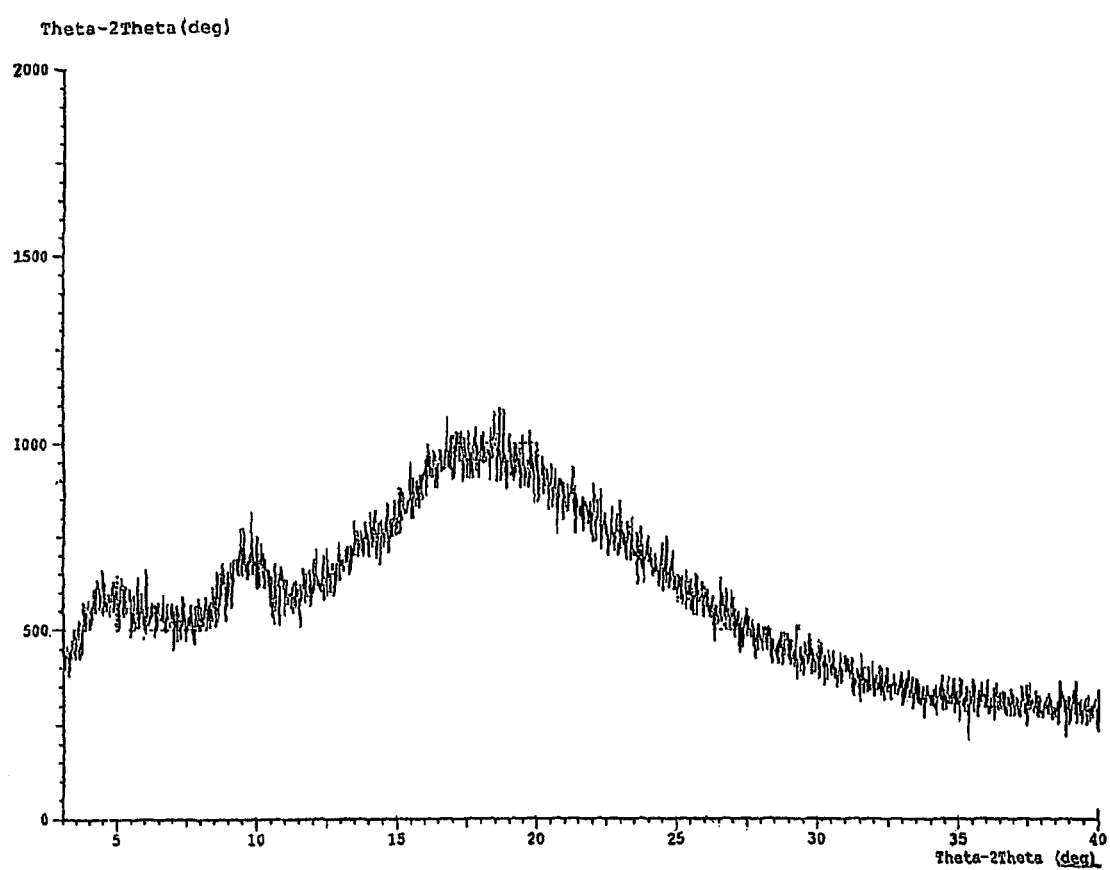

METHOD FOR THE PREPARATION OF MONTELUKAST ACID AND SODIUM SALT THEREOF IN AMORPHOUS FORM

FIELD OF THE INVENTION

This invention relates to an improved method for the preparation of Montelukast acid and its sodium salt The present invention particularly relates to a method for the preparation of amorphous Montelukast sodium. Further, the invention relates to an improved method that is industrially feasible and commercially profitable. More particularly the present invention relates to a method for the isolation of pure crystalline montelukast acid and its subsequent conversion into amorphous montelukast sodium. The conversion is carried out by using a mixture of polar protic and water immiscible nonpolar solvent system. The method results in the production of montelukast sodium in amorphous form with high purity, low residual solvent content and comparable yield.

BACKGROUND OF THE INVENTION

The leukotrienes are potent inflammatory mediators which may have a role in inflammatory diseases such as allergic rhinitis, inflammatory bowel disease and asthma. Biosynthetically, generation of leukotrienes is catalyzed by the calcium and ATP-dependent enzyme 5-lipoxygenase, which metabolise arachidonic acid via the insertion of oxygen moiety at a specific position, into hydroperoxyeicosatetraenoic acids (HPETEs). $LTB_4$, $LTC_4$, $LTD_4$, $LTE_4$ and the cysteinyl leukotrienes (CysLTs) are the clinically important leukotrienes. To synthesize leukotrienes, cells need 5-lipoxygenase and a protein co-factor 5-lipoxygenase activating protein (FLAP) and drugs that act on either of the two inhibit their synthesis and actions. There are two distinct receptor types for the CysLTs ($CysLT_1$ and $CysLT_2$ receptors) and one for $LTB_4$ (BLT receptor). $LTB_4$ is a potent chemotactic agent and attracts pro-inflammatory cells, e.g. eosinophils, into tissues. The CysLTs contract airway and some vascular smooth muscle, stimulate mucus secretion and increase micro vascular permeability. Further details of the leukotrienes are to be found in the book "*Leukotrienes and Lipoxygenase*", ed. J. Rokach, Elsevier, Amsterdam (1989). Rokach also discusses the actions of the leukotrines in living systems and their contribution to various disease states in the book. Montelukast Sodium being a leukotriene antagonist is useful in the treatment of pulmonary disorders including asthma and related obstructive airway diseases, allergies and allergic reactions, inflammation as well as anti-inflammatory agent, skin disorders, cardiovascular disorders, cerebral disorders, uveitis, glomerular, nephritis, hepatitis, and allograft rejection.

Montelukast sodium is chemically described as [R-(E)]-1-[[[1-[3-[2-(7-Chloro-2-quinolinyl ethenyl]phenyl]-3-[2-[(1-hydroxy-1-methylethyl)phenyl]propyl]thio]methyl] cyclopropane acetic acid, sodium salt and is known to be a therapeutically useful compound. Its empirical formula and molecular weight are $C_{35}H_{35}ClNNaO_3S$ and 608.17 respectively. Montelukast sodium displays the structural formula (I). It is a optically active, highly hygroscopic, white to off-white powder, freely soluble in ethanol, methanol and water and practically insoluble in acetonitrile.

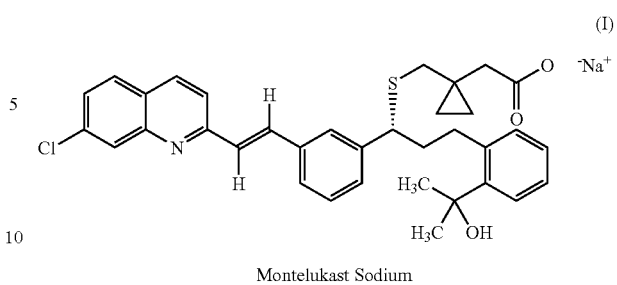

Montelukast Sodium

Synthesis of Montelukast sodium in its amorphous form (Process A—Scheme 1) is fully described by reference to the examples, in U.S. Pat. No. 5,565,473 and European Patent Publication 0, 480, 717.

Synthetic Scheme for Preparing Amorphous Montelukast Sodium as per U.S. Pat. No. 5,565,473

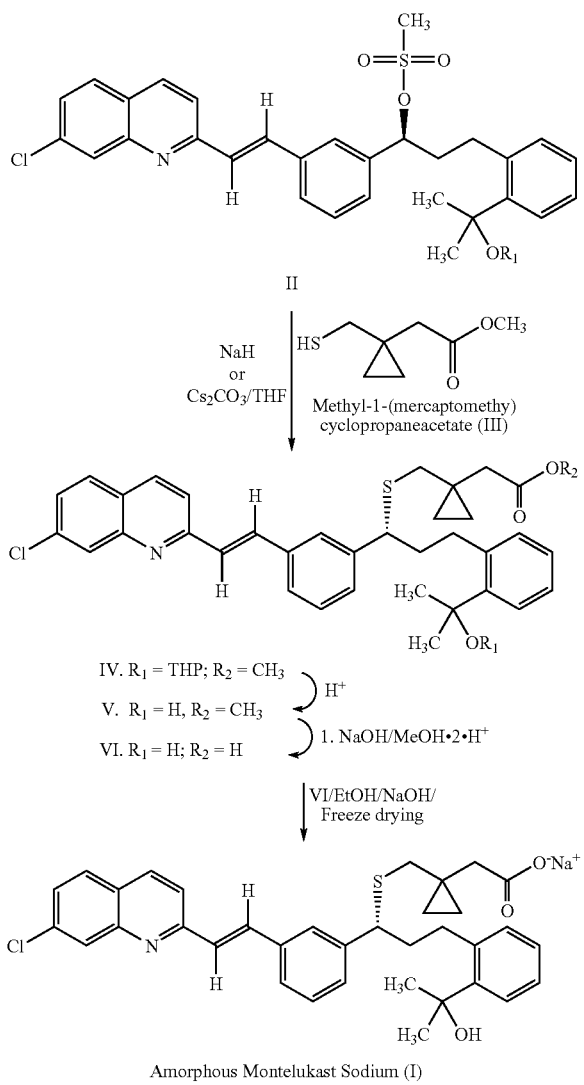

Amorphous Montelukast Sodium (I)

The reported synthesis of (I) proceeds through its corresponding methyl ester (V) whose formation comprises sodium hydride or cesium carbonate assisted coupling of methyl-1-(mercaptomethyl)cyclopropaneacetate (III) with the protected mesylate of formula (II) to afford the protected alcohol ester derivative (IV) followed by its deprotection under acidic conditions. The ester (V) is hydrolyzed to free acid (VI) and then converted directly to sodium salt (I). According to the examples of above cited patents, montelukast acid (VI) in its pure form is first treated with sodium hydroxide in ethanol, the solvent is evaporated under vacuum, the resulting viscous oil is dissolved in water and then freeze-dried. Pure (VI) used was obtained via the hydrolysis of corresponding ester (V) with methanolic sodium hydroxide followed by acidification with dilute acetic acid and finally purified through time consuming column chromatography on silica gel. The process is obviously lengthy as well as tedious since it requires chromatographic purification of both the methyl ester (V) and montelukast acid (VI). Further, it also requires capital-intensive freeze-drying equipment and thus proves to be commercially expensive if not unviable.

As indicated above, the reported syntheses of montelukast acid (VI) proceeds through its corresponding methyl ester (V) and involves coupling of methyl-1-(mercaptomethyl) cyclo propane acetate (III) with a mesylate (II) generated in situ. The methyl ester (V) thus obtained is hydrolyzed to the free acid (VI), which in turn is converted directly to the corresponding sodium salt. The process is not suitable for large-scale production, as it requires tedious chromatographic purification of intermediates and freeze-drying of Montelukast sodium (I).

Moreover, the yields of the intermediates are also low.

U.S. Pat. No. 5,614,632 advocates the preparation of Montelukast sodium in crystalline form. As per detailed description, the process comprises converting 1-(mercaptomethyl) cyclopropaneacetic acid into dilithium dianion by reacting with lithium bases such as n-butyl lithium in hexane or heptane in presence of inert solvents like tetrahydrofuran (THF), toluene, or mixture thereof at sub-zero temperatures and then reacting the said dilithium dianion of 1-(mercaptomethyl) cyclopropaneacetic acid with the mesylate in solid or solution form, in inert organic solvents such as THF or toluene, preferably THF.

The mesylate has limited stability in solution and is therefore preferably prepared just prior to the reaction with the dianion solution. It is isolated in solid form at low temperature and stored at −15° C. over a period of time. The solution can best be used within about 30 minute of its preparation. Optionally, during its preparation, the reaction mixture is seeded with the crystals of mesylate in order to accelerate crystallization of the product. Further, in accordance with the example, the process leads to selective mono mesylation of diol with methanesulphonyl chloride in the presence of sterically hindered base N,N-diisopropylethylamine in a mixture of toluene and acetonitrile. After the addition of methanesulphonyl chloride, the reaction mixture is seeded with crystals of previously prepared mesylate salt to induce crystallization as stated above. The mesylate after careful filtration under nitrogen gas atmosphere at −25° C. is washed successively with chilled acetonitrile (−30° C.) and hexanes (+5° C.) and then dried at +5° C. by passing dry nitrogen gas through it for approximately 20 hrs. This is a risky process requiring capital intensive cold room facility, constant careful handling as accidental rise in temperature during this lengthy drying procedure could either lead to the formation of impurities which may be carried forward to the next stage or result in complete decomposition of the expensive advanced intermediate. The dried mesylate is then coupled with the dianion generated from 1-(mercaptomethyl)cyclopropaneacetic acid and n-butyl lithium (15% solution in hexanes) at −5±2° C. in THF to obtain after workup and recovery of solvents, Montelukast acid in crude form, as a viscous oil. The reaction between dianion and mesylate is allowed to take place at subzero temperatures for about 10 hrs followed by treatment of the reaction mixture with a carboxylic acid, preferably tartaric acid to produce montelukast acid in crude and impure form. The crude acid thus obtained has to be purified through its corresponding salt dicyclo hexyl amine salt (DCHA) produced by reacting the said acid with DCHA in presence of solvent to facilitate crystallization Depending upon the solvent used, two crystalline forms of the DCHA salt are obtained. Form A is crystallized from a mixture of ethyl acetatehexanes and Form B from toluene/heptane. The montelukast DCHA salt, after filtration has to be washed with in a mixture of toluene/n-heptane or ethyl acetate/n-hexane before being converted into crystalline Montelukast sodium (I). The examples also advise seeding with crystals of DCHA salt to accelerate crystallization of the product.

The process as described, teaches that the dicyclohexylamine (DCHA) salt is readily isolable in crystalline form and is advantageously used as means of purification of title product of the invention. The montelukast acid, generated in-situ in toluene, by treating DCHA salt with dilute acetic acid is directly converted into montelukast sodium by reacting with sodium hydroxide and after repeated recovery of solvents is crystallized (after seeding with the difficult to obtain crystals) by slowly adding excess of acetonitrile to the toluene solution at +40±2° C. After the addition of acetonitrile, the slurry of crystalline montelukast sodium is aged for 12 to 16 hrs at +40±2° C. In order to obtain montelukast sodium in pure and crystalline form, the DCHA salt (X) with purity ≧99% is used and seeding plays a very critical role during crystallization.

As is clear from the above discussions, both the routes (Processes A and B) for the synthesis of montelukast sodium suffer from several drawbacks and involve steps that are lengthy, tedious, non-reproducible and require stringent conditions and high capital infrastructure. Additionally, they require intermediates of high purity, which may have to be chromatographically purified. Therefore, there is a need for developing methodologies, which overcome the above mentioned drawbacks.

OBJECTIVES OF THE INVENTION

It is, therefore, an object of the present invention to provide an efficient method for the preparation of Montelukast sodium (I) in amorphous form, which eliminates the major problems associated with the prior arts.

Another object of the present invention is to provide a time and cost effective method for the preparation of montelukast sodium salt (I) in amorphous form.

Yet another object of the present invention is to provide a simple method for the isolation of pure crystalline montelukast acid and its subsequent conversion into montelukast sodium (I) In Amorphous Form.

Still another object of the present invention is to provide a method for the preparation of montelukast acid in crystalline form and montelukast sodium (I) in amorphous form, that is reproducible, convenient to operate on commercial scale.

Further object of the present invention is to provide a method for the preparation of montelukast sodium (I) with high purity particularly in terms of contents of residual solvent in the title compound and consistent quality.

Yet another object of the present invention is to provide a method for the preparation of Montelukast sodium (I) that eliminates cumbersome processes such as freeze-drying and purification by column chromatography.

Still yet further object of the present invention is to provide a method for the preparation of montelukast sodium (I) that avoids lengthy and capital-intensive isolation of thermally unstable and labile mono mesylate and its subsequent storage at sub zero temperatures.

The novelty of the present invention resides in:
(i) coupling predetermined amount of dilithium dianion of 1-(mercaptomethyl)cyclo propane acetic acid prepared from calculated amounts of n-butyl lithium or predetermined amount of the said 1-(mercaptomethyl)cyclo propane acetic acid and alkyl lithium with wet mesylate thereby eliminating the cumbersome time consuming capital intensive process for drying of thermally unstable and labile mesylate,
(ii) isolation of pure montelukast acid in crystalline form from its DCHA salt,
(iii) avoiding seeding or freeze drying of montelukast sodium salt (I) and
(iv) conversion of pure montelukast acid into montelukast sodium (I) in amorphous form thereby eliminating capital intensive and time consuming steps of freeze drying.

The process of the present invention is illustrated with the help of the following figure:

Synthetic Scheme for Amorphous Montelukast Sodium

Scheme 2

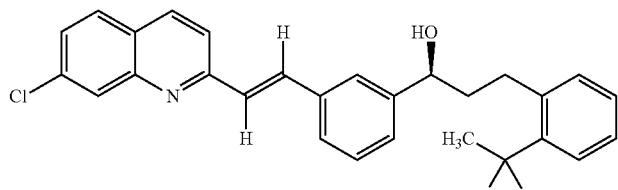

VII

MsCl/DIPEA/Toluene/ACN   -40 to -25° C.

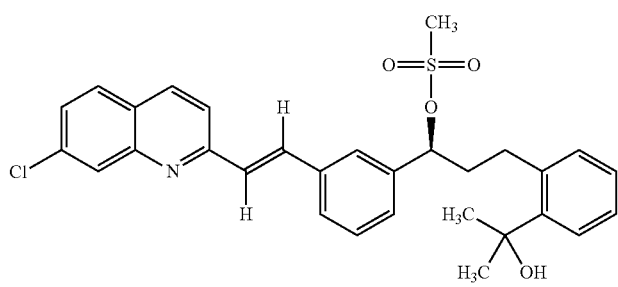

VIII n-BuLi/THF
-10 to -5 ± 2° C.

1-(Mercaptomethyl)cyclopropaneaceticacid (IX)

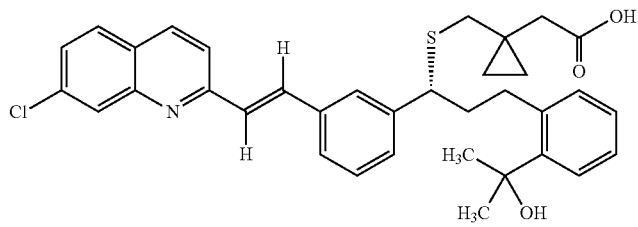

Crude VI

DCHA/EtOAc/Hexanes or
DCHA/EtOAc/Toluene/Hexanes

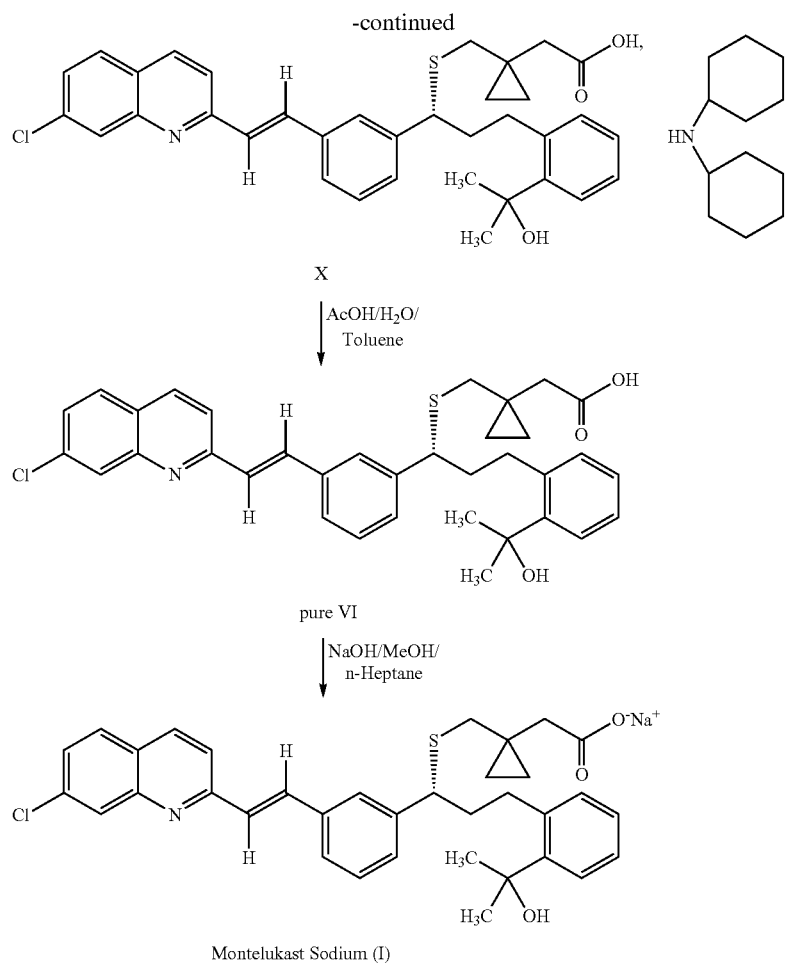

Montelukast Sodium (I)

SUMMARY AND DETAILED DESCRIPTION OF THE INVENTION

Accordingly, the present invention provides an improved method for the preparation of montelukast sodium salt thereof in amorphous form, which comprises:
(a) generating the dilithium dianion of 1-(mercaptomethyl) cyclopropaneacetic acid (IX) by reacting with an alkyl lithium reagent,
(b) coupling the said dianion with wet mesylate of formula (VIII) to obtain montelukast acid (VI) in crude form,
(c) obtaining DCHA salt (X) in crude form by adding N,N-dicyclohexylamine (DCHA) to crude acid obtained in the above step (b),
(d) purifying and converting the said DCHA salt (X) in crude form to montelukast acid (VI) in pure form, and
(e) reacting the pure montelukast acid (VI) in a polar protic solvent with a source of sodium ion followed by evaporating the solvent and triturating of the residue with non-polar water immiscible solvent to obtain the title compound.

According to the present invention, there provides an improved method for the preparation of montelukast acid and sodium salt thereof in amorphous form, which comprises:
(a) coupling the 1-mercaptomethyl)cyclopropaneacetic acid (IX) with mesylate of formula (VIII) in the presence of alkyl lithium base to get montelukast acid (VI) in crude form,
(b) obtaining DCHA salt (X) in crude form by adding N,N-dicyclohexylamine (DCHA) to crude acid (VI) obtained in the above step (a),
(c) purifying and converting the said DCHA salt (X) in crude form, to montelukast acid (VI) in pure form, and
(d) reacting the pure montelukast acid (VI) in a polar protic solvent with a source of sodium ion followed by evaporating the solvent and triturating the residue with non-polar water immiscible solvent to obtain the title compound.

One of the embodiment of the present invention is that the dianion of the present invention is generally, but not limited to, prepared according to the process described in the U.S. Pat. No. 5,614,632.

Other embodiment of the present invention is that the alkyl lithium used may be such as methyl, ethyl, propyl, butyl, isobutyl, tertiary butyl, n-pentyl or n-hexyl lithium.

Another embodiment of the present invention is that the mesylate (VIII) is prepared by reacting corresponding diol (VII) with methanesulphonyl chloride. The reaction may be carried out in an inert organic solvent like toluene, acetonitrile, or mixture thereof or THF or DMF in presence of tertiary amine such as N,N-diisopropylethylamine (DIPEA). The reaction is conducted at −50 to −15° C., for about 5-6 hrs. The preferred conditions for selective mono mesylation at the secondary hydroxy group are: toluene in combination with acetonitrile as solvent with a preferred ratio of 1:2 to 1:3, reaction temperature range between −40 to −25° C. preferably between −30 to −15° C. with DIPEA as the base.

In one part of the improvement in the present invention, we have over come the risk of formation of impurities and decomposition during the long time drying of the intermediate mesylate (VIII) under nitrogen blanket at sub zero temperatures, before coupling with dilithium dianion of (IX) by performing the reaction with the wet compound. In the modified process, a portion of the wet mesylate (VIII) after filtration under atmosphere of nitrogen gas and drying under vacuum for a very short time of 5-10 minutes is immediately subjected to loss on drying (LOD) analysis of the residual solvents trapped in the crystals. Based on the LOD results, the dry weight of mesylate (VIII) formed is determined and subsequently quantities of alkyl lithium in hexanes and 1-(mercaptomethyl)cyclopropane acetic acid (IX) to be used during reaction are calculated. The extent of solvent trapping in the crystals of (VIII) may vary between 5-50% or more as has been observed in laboratory experiments and LOD analysis. In some of the samples of (VIII), even longer (0.5-1.0 hr) drying under vacuum at 0 to +5° C. did not result in appreciable reduction in LOD analysis, which indicates the tendency of the powder to trap the solvents. After correction in weight, the wet mesylate (VIII) is as such immediately used for coupling with the dilithium dianion of (IX). The terms "wet mesylate (VIII) or wet (VIII)" mentioned anywhere in the text specifically implies filtered samples of (VIII) in which the combined percentage (w/w) of trapped organic solvents may vary between 5 to 50 or more.

Yet another embodiment of the invention is the manner in which coupling between the dilithium dianion of (IX) and mesylate (VIII) is effected. The reaction may be carried out in inert organic solvent(s) at a temperature below 0° C. First 1-(mercaptomethyl) cyclopropaneacetic acid (IX) is converted to its dilithium salt by reacting with alkyl butyl lithium in hexanes at −30 to 0° C., preferably at −15 to −10° C. in inert organic solvent preferably in THF and then coupled with wet mesylate (VIII) at −30 to +30° C. preferably at −10 to −03° C. Both n-butyl/alkyl lithium [0.15 molar (1.0%) to 4.0 molar (25%) solution in hexanes] and 1-(mercaptomethyl)cyclopropaneacetic acid (IX) in THF could be used in 2.0 to 3.50 molar equivalence and 1.0 to 1.50 molar equivalence respectively. In the most appropriate and suitable experimental condition, 2.20-2.40 molar equivalents of n-butyl lithium in hexanes (10% solution/1.60 molar) and 1.20 molar equivalents of (IX) are used for coupling with wet mesylate (VIII) whose yield has been calculated on dry basis after LOD analysis. The coupling may be carried out in inert organic solvent like tetrahydrofuran over a period of 1 to 18 hrs. n-butyl lithium can be substituted by alkyl lithium.

The coupling may be accomplished in the following embodiments:

a. Slow addition of a cooled (−30 to +5° C.) solution of wet (VIII) in THF to a cooled (−30 to +5° C.), stirred and mixed solutions of (IX) and n-butyl lithium in hexanes and THF.

b. Slow addition of n-butyl lithium in hexanes (−30 to +35° C.) to a cooled (−30 to +5° C.), stirred and mixed solutions of wet (VIII) and (IX) in THF.

c. Slow addition of cooled (−30 to +5° C.) solution of (IX) to a cooled (−30 to +5° C.), stirred and mixed solutions of wet (VIII) and n-butyl lithium in THF and hexanes.

d. Slow addition of a cooled (−30 to +5° C.) solution of a mixture of (IX) and n-butyl lithium in hexanes and THF to a cooled (−30 to +5° C.) and stirred solution of wet (VIII) in THF.

e. Slow addition of a cooled (−30 to +5° C.) solution of a mixture of (VIII) and (IX) to a cooled (−30 to +5° C.) and stirred solution of n-butyl lithium in hexanes and THF.

f. Slow addition of a cooled (−50 to −25° C.) solution of a mixture of (VIII) and n-butyl lithium in THF and hexanes to a cooled (−30 to +5° C.) and stirred solution of (IX) in THF.

g. Parallel and concurrent slow addition of solutions of n-butyl lithium (−30° to +35° C.) in hexanes and (IX) (at −30 to +35° C.) in THF to a cooled (−30 to +5° C.) solution of wet (VIII) in THF.

h. Parallel and concurrent slow addition of solutions of n-butyl lithium (−30 to 35° C.) in hexanes and a cooled solution (−30 to +5° C.) of wet (VIII) in THF to a cooled and stirred solution (−30 to +5° C.) of (IX) in THF.

i. Parallel and concurrent slow addition of a cooled (−35 to +5° C.) solution of (VIII) in THF and (IX) in THF (+30 to +35° C.) to a cooled (−30 to +5° C.) and stirred solution of n-butyl lithium in hexanes and THF.

In all the above reaction conditions, the progress of the reaction is monitored by TLC over a period of 1 to 18 hrs at −30 to +30° C., preferably at −20 to 0° C.

The most suitable and appropriate condition for coupling is the one wherein the reaction mixture is stirred for 12-16 hrs at −10 to −3° C.

After aqueous workup and recovery of solvents, the montelukast acid (VI) in crude form could not be crystallized from solvents and is purified via its DCHA salt (X) formation by reacting with N,N-dicyclohexylamine (DCHA). Two methods were developed for crystallizing the DCHA salts. In the first method (Method A), the thick white to off white slurry of DCHA salt (X) formed by adding DCHA to crude (VI) in ethyl acetate at +25 to +35° C. after filtration is successively washed with ethyl acetate and hexanes at +25 to 35° C. to obtain montelukast DCHA salt (X) as a white to off white solid with a HPLC purity of ~96.0 to 98.5%. The quantity of ethyl acetate used for crystallization of (X) and that of ethyl acetate and hexanes used for washing it may vary between 2-8 times v/w, 0.5-1.5 times v/w and 5-15 times v/w respectively w. r. t. crude (VI) used. Preferably 3-4 times v/w, 0.75-1.25 times v/w and 8-10 times v/w of the respective solvents are used. The purity of DCHA salt (X) is increased to 99.0-99.5%, (Method B) by adding toluene to the thick slurry [of (X) formed above] in ethyl acetate followed by slurry washing of the filtered solid with toluene and finally washing with hexanes at +25 to +35° C. and drying under vacuum. The quantity of toluene that is added to the reaction mixture of (X) may vary between 2-10 times v/w w. r. t crude (VI), but 4-6 times is most appropriate. Slurry washing of the filtered crude DCHA salt may be performed with 5-25 times v/w of toluene but 8-10 times is most appropriate. For both the methods A and B, the reaction temperature may vary between +5 to +50° C. but is preferably performed at +25 to +35° C. The duration of the reaction may vary between 2-24 hrs but 10-14 hrs is most appropriate for both the methods A and B.

In the next stage of the embodiment, a suspension of dried DCHA salt (X) in a mixture of water and organic solvent is treated with dilute acid for 15 to 20 minutes at +10 to +40° C. The acid could be organic or inorganic and its concentration may range between 0.1M to 10M. The organic acid that could be used are acetic acid, n-propionic acid, isopropionic acid, n-butyric acid, isobutyric acid or any long chain acids where $C \cong 8$. The inorganic acids employed could be hydrochloric acid, hydrobromic acid, hydroiodic acid, hydrofluoric acid, sulfuric acid, nitric acid, phosphoric acid and polyphosphoric acid. The acids may be used in pure form or as mixtures in a suitable proportion and even mixtures of organic and inorganic acids could be used. However, depending upon the type of organic solvent being used for the above transformation, the process of crystallization and isolation has to be modified in order to obtain the montelukast acid (VI) in pure form.

In general, a suspension of DCHA salt (X) in a mixture of water and water inmiscible organic solvent is stirred with a dilute solution of acid. The quantity of organic solvent and water used may vary between 10-40 times v/w w. r. t (X) in 1:1 to 1:3 ratio preferably 25-30 times in 1:1 ratio is used. As much quantity of dilute acid (preferably 2M solution) is also used to bring the pH of the mixture down to around 4-6 and the reaction is preferably performed at +25 to +35° C. The organic layer is separated, washed with water and the precipitated montelukast acid (VI) in pure form is filtered off. Toluene, benzene, ortho and para xylenes, methyl acetate and ethyl acetate are the solvents of choice.

Alternatively, the treatment of (X) with dilute acids could also be performed in a mixture of water immiscible halogenated polar solvents like dichloromethane, chloroform, and 1,2-dichloroethane in which the resulting montelukast acid (VI) is partially soluble. However, after separation of aqueous layer, the organic layer is washed with water and evaporated to $\frac{1}{3}^{rd}$-$\frac{1}{4}^{th}$ of its volume and then crystallized by adding solvents like cyclopentane, n-pentane, cyclohexane, n-hexane, hexanes, cycloheptane, heptanes, n-heptane, diethyl ether, diisopropyl ether, dibutyl ether, tertiary butyl methyl ether, benzene, toluene, ortho and para xylenes, methyl acetate and ethyl acetate. The solvents may be used in pure form or as mixtures in a suitable composition. Moreover, the halogenated solvent can also be completely recovered and residue thus obtained is simply stirred with organic solvents like benzene, toluene, ortho and para xylenes, diethyl ether, diisopropyl ether, tertiary butyl methyl ether, methanol, ethanol, n-propanol, isopropanol, n-butanol, isobutanol etc. at +10 to +40° C., preferably at +25 to +35° C. and filtered to obtain montelukast acid (VI) in pure form.

In another embodiment of the invention, the above reaction can also be performed in mixture of water and water miscible solvents like methanol, ethanol, n-propanol, isopropanol, n-butanol, isobutanol, tetrahydrofuran, 1,2-dimethoxyethane, 1,2-diethoxyethane, acetonitrilie, dimethylformamide, dimethylacetamide and dimethyl sulfoxide. After the reaction is over, charging of additional amount of water leads to precipitation of pure (VI), which is then filtered off and dried. Alternatively, after the addition of water, the reaction mixture is extracted with excess of organic solvents like methylene chloride, chloroform, 1,2-dichloroethane, methyl acetate, ethyl acetate, benzene, toluene or ortho and para xylenes, the organic layer is separated, washed with water, dried and evaporated to obtain pure (VI) either directly after filtration or crystallized after addition of common non polar aliphatic and alicyclic organic solvents like cyclopentane, n-pentane, and their higher homologues as mentioned above. The solvents may be used in pure form or as mixtures during reaction, extraction or crystallization.

In general, by using the above reaction conditions, the DCHA salt (X) obtained by using method A provide (VI) which display HPLC purity between 96.-98.5% and that obtained from method B show purity (HPLC) above 99.50%.

When the acidification of (X) with dilute acids is performed in common aliphatic and alicyclic non polar solvents like, cyclopentane, n-pentane, or their higher homologues where C≅8, and ethers like diethyl ether, diisopropyl ether, dibutyl ether, tertiary butyl methyl ether etc., the crystalline montelukast acid (VI) is immediately obtained after the reaction is over and can be straightaway filtered off and dried. However, here the compound (VI) obtained is not very pure (HPLC purity ≈95.0-96.0%) if (X) with a purity of 96-98% (obtained via Method A mentioned above) is used and has to be purified by re-crystallization from ethyl acetate or any other appropriate solvents. Use of (X) with a purity of ≧99% (obtained via Method B mentioned above) provides pure (VI), which displays HPLC purity of ≧99.0% and can be directly converted into pure amorphous montelukast sodium (I) as mentioned above in the text. Here too, the solvents may be used in pure form or as mixtures while performing the reaction or during purification of (VI).

In the most appropriate embodiment of the above transformation, a suspension of crude DCHA salt (X) in toluene and water is treated with 2M acetic acid at +25 to +35° C. for 15-20 min., the organic layer is separated, washed with water and stirred at +25 to +35° C. for 6-8 hrs. The resulting light pale yellow crystals of pure (VI) are filtered and dried under vacuum. The optimum ratio of (X): 2M acetic acid: Toluene: Water is 1:1:10:10. Analysis of the data given in the experimental section/Table I indicates that samples of DCHA salts (X) prepared via method B provide pure (VI) of superior quality than those prepared using method A.

Finally, the purified montelukast acid (VI) is dissolved at ambient temperature preferably in lower aliphatic alcohols like methanol or ethanol and reacted with 1.05 to 1.10 molar equivalents of sodium hydroxide to form a solution of sodium salt of montelukast. The solvent is evaporated under high vacuum at +5 to +50° C., most appropriately at +35 to +40° C. The viscous oily or foamy solid that is formed after the evaporation of alcoholic solvent is triturated with non polar solvents like cyclopentane, n-pentane, cyclohexane, n-hexane, cycloheptane, or n-heptane, at 0 to +50° C., most appropriately at +25 to +35° C. and stirred for 0.5 to 6 hrs, preferably for 1 to 2 hrs. The solid is filtered off and dried <+40° C. under vacuum to obtain pure montelukast sodium (I) as a white amorphous powder. All the synthesized samples of (I) displayed very high purity as well as assay and low levels of residual solvent contents as shown in Table II in the experimental section.

The invention is further defined by reference to the following example, which is intended to be illustrative. The examples are not meant to limit in any manner the effective scope of the invention as herein defined and claimed. Consequently, any variation of the invention described above is not to be regarded as departure from the scope of the invention claimed. The invention has been described in terms of its embodiments and certain modifications and equivalents as will be apparent to those skilled in the art and are intended to be included within the scope of present invention. Further the invention is also described with reference to the drawing accompanying this specification FIG. 1 in which depicts X-ray powder diffractogram (XRD) of montelukast sodium in amorphous form.

All the chemicals used were of commercial grade and were analyzed before use. IR spectra were recorded on NICOLET-AVATAR 320 FT-IR spectrophotometer and $^1H/^{13}C$-NMR spectrum measurements were made on BRUKER DPX-300 spectrometer at ambient temperature. Electron Ionization Mass Spectrum (EIMS) and Atmospheric Pressure Chemical Ionization Mass Spectrum (APCI-MS) were recorded on VG-70-250S and FINNIGAN MATT LCQ mass spectrometers respectively. CHNS elemental analysis were estimated using Elementar Analysen Systeme GmbH VARIO EL CHNS Elementar Analyser. Powder X-Ray Diffraction (XRD) analysis was carried out on SHIMADZU XRD-6000 instrument

EXAMPLE-1

[(S)-(E)]-2-[2-[3-[3-[2-(7-Chloro-2-quinolinyl)ethenyl]phenyl]3-methanesulphonyloxy]propyl]phenyl]-2-propanol (VIII)

To a 2.0 lt./4 neck round bottom flask fitted with a mechanical stirrer and thermometer inlet were successively charged diol (VII) (75.0 g, 0.16 mol), toluene (225 ml) and acetonitrile (600 ml) under an atmosphere of nitrogen gas at +25 to +35° C. After stirring for approximately 10 minutes, N,N-diisopropylethylamine (23.29g/30.90 ml, 0.18 mol) was added over a period of 5 minutes. The solution was cooled to −30 to −25° C. in a liquid $N_2$/methanol bath, methanesulphonyl chloride (33.0g/22.5 ml, 0.29 mol) was added drop wise over a period of 15 minutes, keeping the temperature at −30 to −25° C. and stirred for 5 hrs at this temperature. During this period, thick off white to pale yellow solid had precipitated out. The reaction mixture was further cooled to −30 to −40° C., product (VIII) was carefully filtered, successively washed with chilled acetonitrile (−30° C., 75 ml.) and chilled hexanes (−15° C., 150 ml) under nitrogen gas atmosphere and suck dried for approximately 5-10 minutes at −5 to 0° C. After LOD analysis, the filtered (VIII), obtained as off white to pale yellow powder, was immediately used as such in wet condition in the next step without further drying.

Yield of wet (VIII)=148.0 g (LOD=46.50% w/w).

Yield on dry basis (corrected after LOD analysis)=79.18 g. (90.21%).

EXAMPLE-2

[(R)-(E)]-1-[[[-1-[3-[2-(7-Chloro-2-quinolinyl)ethenyl]phenyl]-3-[2-(1-hydroxy-1-methyl ethyl)phenyl] propyl]thio]methyl]cyclopropaneacetic acid dicyclohexylamine salt (X)

Step 1 n-Butyl lithium (195 ml, 1.6 Molar solution in hexanes, 0.312 mol.) was slowly added to a cooled (−15 to −10° C.) solution of 1-(mercaptomethyl)cyclopropaneacetic acid (IX) (23.25 g, 0.16 mol.) in dry THF (385 ml.) in a 1 lt./4 neck round bottom flask fitted with a mechanical stirrer and a thermometer inlet under nitrogen atmosphere and the mixture was stirred for 30 minutes at −15 to −10° C.

Step 2

To a separate a 1.0 lt/4 neck round bottom flask equipped with a mechanical stirrer, thermometer inlet and under dry nitrogen gas atmosphere was placed THF (385 ml) and the solvent was cooled to −10 to −5° C. The wet monomesylate (VIII) (77.0 g, 0.144 mol/amount calculated on dry basis after LOD analysis) was added via a powder funnel and the mixture was stirred for 15 minutes at −10 to −5° C. to ensure complete dissolution to obtain a clear pale yellow solution.

Step 3

The solution of mesylate (VIII) in THF at −10 to −5° C. (from step 2 above) was slowly added to the dianion slurry of (IX) (step 1 above) at −15 to −10° C. via addition funnel under nitrogen gas atmosphere over a period of 30 minutes. The reaction mixture was stirred at −5±2° C. for 12 hrs when the TLC of the reaction indicated it to be complete. Aqueous 10% sodium chloride solution (225 ml.) was added slowly to quench the reaction, the organic layer was separated, the aqueous layer was extracted with ethyl acetate (300 ml.) and the combined organic layers were successively washed with 10% tartaric acid solution (2×188 ml) and water (4×188 ml). The organic layer was stirred with activated charcoal and anhydrous sodium sulphate for 30 minutes at +25 to +35° C. and filtered through hyflo-bed. Complete recovery of solvent <40° C. under vacuum provided crude (VI) as a pale yellow viscous oil which was used as such in the next stage.

Yield of crude (VI)=75.0 g.

Step 4

Two methods were used for synthesizing the Montelukast DCHA salt (X).

Method-A

To a stirred solution of crude montelukast acid (VI) (75.0 g, 0.13 mol.) dissolved in ethyl acetate (300 ml) in a 1.0 lt./4 neck round bottom flask equipped with a mechanical stirrer, a thermocouple and addition funnel at +25 to +35° C., neat N,N-dicyclohexylamine (52.50 ml, 0.26 mol.) was slowly added at over 30 minutes. The reaction mixture was stirred for 30 minutes at +25 to +35° C. and seeded with crystals of DCHA salt (X). The mixture was further stirred for approx 10-12 hrs at +25 to +35° C. during, which time thick white to off white solid precipitates out. Additional ethyl acetate (225 ml) was added to the reaction mass and stirred for 1 hr. The solid was filtered, successively washed with ethyl acetate (75 ml), hexanes (675 ml.) at +25 to +35° C. and dried under vacuum at +40 to +45° C. for approx. 6 hrs to obtain montelukast DCHA salt (X) as a white to off white solid. Yield=80.50 g; Purity (HPLC)=98.06%; Assay (HPLC)=97.52%; Melting point=113-117° C.

Method B

To the thick white to off-white slurry of DCHA salt (X) obtained from crude Montelukast acid (VI) (75.0 g), ethyl acetate (300 ml) and N,N-dicyclohexylamine (52.50 ml), toluene (375 ml) was added and the mixture was stirred for 10-12 hrs at +25 to +35° C. Filtration followed by slurry washing with toluene (300 ml), followed again by filtration, washing with hexanes (300 ml) and drying under vacuum afforded Montelukast DCHA salt (X) as a white to off white powder. Yield=84.0 g; Purity (HPLC)=99.73%; Assay (HPLC)=99.32%; Melting point=113-116° C.

EXAMPLE-3

[(R)-(E)]-1-[[[-1-[3-[2-(7-Chloro-2-quinolinyl)ethenyl]phenyl]-3-[2-(1-hydroxy-1-methylethyl)phenyl] propyl]thio]methyl]cyclopropaneacetic acid (Pure VI)

To a stirred suspension of montelukast DCHA salt (X) (80.0 g, 0.104 mol, purity 98.06%, assay=97.50.%), in toluene (800 ml.) and DM water (800 ml.) at +25 to +35° C., acetic acid (2.0 Molar soln., 80 ml.) was charged over a period of 30 minutes and the mixture was stirred for another 15 minutes at +25 to +35° C. The toluene layer was separated, washed with water (800 ml). The toluene layer was separated, seeded with crystals of pure (VI) and stirred at +25 to +35° C. for 5-6 hrs. The resulting solid was filtered, washed with toluene (160 ml) and dried at +40 to +45° C. under vacuum to yield pure montelukast acid (VI) as a light yellow solid. Yield=37.0 g (60.54%); Purity (HPLC)=98.95%; Assay (HPLC)=99.01%; Melting point=148-150° C.

IR (KBr, $cm^{-1}$)=3573.1, 2988.2, 2919.6, 1716.0, 1606.7, 1500.1, 1407.8, 1076.0, 842.3, 766.2, 698.8.

$^1$H-NMR (300 MHz, $CDCl_3$), δ (ppm)=0.40-0.56 (bd, 4H, cyclopropyl H); 1.58 (s, 3H, $CH_3$); 1.59 (s, 3H, $CH_3$); 2.14-2.63 (m, 6H, S—$\underline{CH_2}$—$C_3H_4$, and —$\underline{CH_2}$—$CO_2H$, S—CH—CH$_2$—CH$_2$); 2.84-2.94 (m, 1H, S—CH—CH$_2$—CH$_2$); 3.11-3.21 (m, 1H, S—CH—CH$_2$—CH$_2$); 3.96-4.01 (t, 1H, S—CH—CH$_2$—CH$_2$); 7.07-8.05 (m, 15H, aromatic H).

$^{13}$C-NMR (75.47 MHz, CDCl$_3$), δ (ppm)=12.43 (cyclopropyl CH$_2$); 12.72 (cyclopropyl CH$_2$); 16.84 (cyclopropyl C); 31.63 (CH$_3$); 32.32 (S—CH—CH$_2$—CH$_2$), 39.01 (S—CH—CH$_2$—CH$_2$); 39.96 (S—CH$_2$—C$_3$H$_4$); 40.26 (CH$_2$—CO$_2$H); 50.36 (S—CH—CH$_2$); 73.66 ((CH$_3$)$_2$=C—OH); 119.19, 125.44, 125.33, 126.43, 126.75, 127.17, 127.24, 127.60, 128.42, 128.70, 129.04, 131.54, 135.58, 135.80, 136.46, 140.16, 143.64, 145.29, 148.12, 156.96 (Olefinic and aromatic C); 176.46 (C=O).

EIMS, m/z=586 (M$^+$)

Elemental analysis for C$_{35}$H$_{36}$ClNO$_3$S

| Element | Theoretical (%) | Obtained (%) |
|---|---|---|
| C | 71.70 | 71.86 |
| H | 06.20 | 06.46 |
| N | 02.38 | 02.19 |

EXAMPLE-4

(R)-(E)-1-[[[-1-[3-[2-(7-Chloro-2-quinolinyl)ethenyl]phenyl]-3-[2-(1-hydroxy-1-methylethyl)phenyl]propyl]thio]methyl]cyclopropaneacetic acid; sodium salt (I)

To a stirred and cooled (0 to −5° C.) solution of sodium hydroxide (3.6 g, 0.09 mol.) in methanol (250 ml), pure montelukast acid (VI) (50 g, 0.085 mol) was slowly added in small lots. After stirring at 0 to −5° C. for 30 minutes, the temperature of the reaction mixture was raised to +25 to +35° C. and stirred for 30 minutes. Activated charcoal (1.25 g) was added to the clear pale yellow solution and after stirring for 1 hour at +25 to +35° C., the mixture was filtered through a high-flow-bed and washed with methanol (50 ml). Methanol was then carefully evaporated under vacuum <40° C. and the residue was stirred with n-heptane (400 ml) for 1.5 hr at +25 to +35° C. The white solid was carefully filtered under nitrogen gas atmosphere, washed with n-heptane (100 ml) and dried at +35 to +40° C. under vacuum to obtain Montelukast sodium (I) as a very hygroscopic white powder and stored in closed contained under nitrogen gas atmosphere away from exposure of light. The powder XRD analysis of the sample indicated it to be amorphous (FIG. 1) and XRD data is given below.

Strongest 3 peaks

| peak no. | 2Theta (deg) | d (A) | I/I1 | FWHM (deg) | Intensity (Counts) | Integrated (Counts) |
|---|---|---|---|---|---|---|
| 1 | 21 | 17.2000 | 5.15129 | 100 | 0.00000 | 76 | 0 |
| 2 | 24 | 18.3800 | 4.82315 | 100 | 0.00000 | 76 | 0 |
| 3 | 20 | 16.7000 | 5.30438 | 92 | 0.00000 | 70 | 0 |

Peak Data List

| peak no. | 2Theta (deg) | d (A) | I/I1 | FWHM (deg) | Intensity (Counts) | Integrated (Counts) |
|---|---|---|---|---|---|---|
| 1 | 3.9400 | 22.40794 | 45 | 0.48000 | 34 | 1365 |
| 2 | 4.3400 | 20.34354 | 71 | 0.00000 | 54 | 0 |
| 3 | 4.8800 | 18.09356 | 57 | 0.00000 | 43 | 0 |
| 4 | 5.2800 | 16.72370 | 54 | 0.40000 | 41 | 1443 |
| 5 | 5.7600 | 15.33109 | 28 | 0.00000 | 21 | 0 |
| 6 | 6.1600 | 14.33643 | 24 | 0.00000 | 18 | 0 |
| 7 | 6.3600 | 13.88604 | 21 | 0.44000 | 16 | 537 |
| 8 | 8.8600 | 9.97267 | 42 | 0.56000 | 32 | 1037 |
| 9 | 9.1600 | 9.64672 | 50 | 0.00000 | 38 | 0 |
| 10 | 9.4400 | 9.36121 | 82 | 0.00000 | 62 | 0 |
| 11 | 9.8200 | 8.99980 | 74 | 0.00000 | 56 | 0 |
| 12 | 10.1200 | 8.73367 | 59 | 0.52000 | 45 | 1288 |
| 13 | 10.8208 | 8.16956 | 25 | 0.29170 | 19 | 307 |
| 14 | 13.5600 | 6.52479 | 28 | 0.48000 | 21 | 573 |
| 15 | 14.0000 | 6.32070 | 28 | 0.52000 | 21 | 538 |
| 16 | 15.0200 | 5.89368 | 34 | 0.38000 | 26 | 1022 |
| 17 | 15.4800 | 5.71957 | 49 | 0.00000 | 37 | 0 |
| 18 | 16.1000 | 5.50068 | 82 | 0.00000 | 62 | 0 |
| 19 | 16.3800 | 5.40728 | 76 | 0.00000 | 58 | 0 |
| 20 | 16.7000 | 5.30438 | 92 | 0.00000 | 70 | 0 |
| 21 | 17.2000 | 5.15129 | 100 | 0.00000 | 76 | 0 |
| 22 | 17.6200 | 5.02944 | 82 | 0.00000 | 62 | 0 |
| 23 | 17.8200 | 4.97344 | 84 | 0.00000 | 64 | 0 |
| 24 | 18.3800 | 4.82315 | 100 | 0.00000 | 76 | 0 |
| 25 | 18.8800 | 4.69653 | 75 | 0.00000 | 57 | 0 |
| 26 | 19.1000 | 4.64293 | 67 | 0.00000 | 51 | 0 |
| 27 | 19.3200 | 4.59055 | 72 | 0.00000 | 55 | 0 |
| 28 | 19.5600 | 4.53476 | 64 | 0.00000 | 49 | 0 |
| 29 | 19.7800 | 4.48482 | 70 | 0.00000 | 53 | 0 |
| 30 | 20.2800 | 4.37536 | 62 | 0.00000 | 47 | 0 |
| 31 | 20.7200 | 4.28343 | 38 | 0.00000 | 29 | 0 |
| 32 | 20.9000 | 4.24695 | 39 | 0.00000 | 30 | 0 |
| 33 | 21.1600 | 4.19535 | 42 | 0.00000 | 32 | 0 |
| 34 | 21.6000 | 4.11087 | 30 | 0.00000 | 23 | 0 |
| 35 | 22.0200 | 4.03340 | 32 | 0.00000 | 24 | 0 |
| 36 | 22.2800 | 3.98692 | 28 | 0.14000 | 21 | 348 |
| 37 | 22.7400 | 3.90730 | 21 | 0.68000 | 16 | 371 |
| 38 | 22.9200 | 3.87702 | 24 | 0.00000 | 18 | 0 |
| 39 | 23.2200 | 3.82760 | 26 | 0.45600 | 20 | 485 |
| 40 | 23.8833 | 3.72278 | 20 | 0.44670 | 15 | 336 |
| 41 | 24.5900 | 3.61736 | 28 | 0.34000 | 21 | 450 |
| 42 | 26.6000 | 3.34841 | 22 | 0.24000 | 17 | 399 |

Yield=51.40 g; Purity (HPLC)=98.95%; Assay (HPLC)=98.70%

IR (KBr, cm$^{-1}$)=3396.86, 2970.03, 2925.71, 1636.40, 1594.40, 1570.72, 1495.92, 1406.01, 1068.09, 836.20, 759.92, 697.40.

$^1$H-NMR (300 MHz, CDCl$_3$), δ (ppm)=0.15-0.21 (bd, 2H, cyclopropyl CH$_2$); 0.39 (bd, 2H, cyclopropyl CH$_2$); 1.50 (s, 3H, CH$_3$); 1.54 (s, 3H, CH$_3$); 2.07-2.24 (bm, 4H, S—CH—CH$_2$—CH$_2$); 2.29-2.50 (dd, 2H, S—CH$_2$—C$_3$H$_4$—CH$_2$); 2.70 (bt, 1H, S—CH—CH$_2$—CH$_2$); 3.23 (bt, 1H, CH$_2$—CO$_2$H; 4.53 (bs 1H, CHH$_2$—CO$_2$H); 6.96-7.97 (m, 15H, olefinic and aromatic H).

$^{13}$C-NMR (75.47 MHz CDCl$_3$), δ (ppm)=11.94 (cyclopropyl CH$_2$); 13.12 (cyclopropyl CH$_2$); 17.26 (cyclopropyl C); 31.65 (2 CH$_3$); 32.15 (S—CH—CH$_2$—CH$_2$); 39.55 (S—CH—CH$_2$—CH$_2$); 40.05 (S—CH$_2$—C$_3$H$_4$); 43.60 (CH$_2$—CO$_2$H); 49.73 (S—CH—CH$_2$—CH$_2$); 73.23 ((CH$_3$)$_2$—C—OH); 119.25, 125.49, 125.58, 125.69, 126.99, 128.12, 128.54, 128.64, 128.93, 131.50, 135.15, 135.43, 136.01, 136.46, 140.41, 143.92, 145.33, 148.56, 156.63 (Olefinic and aromatic C); 180.45 (C=O).

APCI-MS MH$^+$=586 [(M+1)−23]

By using the above identical experimental conditions [i.e. from (X) to Pure (VI)], two samples of pure (VI) were prepared from Montelukast DCHA salt (X) (synthesized via Method B) and the data is given in Table-I

TABLE I

| Sl. No. | Quality of (X) used | | | Yield of Pure (VI) (g) (%) | Quality of (VI) | |
|---|---|---|---|---|---|---|
| | Quantity of (X) used (g) | HPLC purity (%) | HPLC Assay (% w/w) | | HPLC purity (%) | HPLC Assay (% w/w) |
| 1. | 84.0 | 99.73 | 99.32 | 42.20 (65.76) | 99.48 | 99.66 |
| 2 | 80.0 | 99.55 | 99.29 | 39.32 (64.33) | 99.52 | 99.68 |

Data for Samples of Amorphous Montelukast Sodium (I) Synthesized from Pure (VI).

TABLE II

| Sl. No | #Quantity of pure (VI) used (g) | Solvent used for salt formation | Yield of (I) (g) (%) | Quality of (I) | | Residual Solvents (ppm) |
|---|---|---|---|---|---|---|
| | | | | HPLC Purity (%) | HPLC Assay (%) | |
| 1. | 50.00 | Methanol | 51.20 (98.70) | 99.42 | 98.90 | Methanol = ND n-Heptane = 38 Toluene = ND |
| 2 | 120.00 | Methanol | 123.00 (98.79) | 99.44 | 99.66 | Methanol = 2087 n-Heptane = ND Toluene = ND |
| 3 | 50.00 | Ethanol | 51.00 (98.30) | 99.64 | 98.60 | Ethanol = 2739 Toluene = ND n-Heptane = 771 |

The samples of pure Montelukast acid (VI) used displayed purity and assay ≧99.50% and were prepared from DCHA salts (X), (HPLC purity ≧99.50%, HPLC assay ≧99.0%) that had been obtained via Method B.
*Solvent used for crystallization of Montelukast sodium (I) after the evaporation of alcoholic solvent in all the experiments was n-Heptane
ND = Not Detected Advantages:
The process is:
(1) Simple as well as time and cost effective.
(2) Industrially feasible and commercially profitable
(3) convenient to operation on commercial scale.
(1) Results in the production of title compound with high yields and purity.
(2) Eliminates requirements of stringent process conditions and sophisticated capital-intensive infrastructure.
(3) Avoids tedious chromatographic purification, isolation of advanced intermediates as well as long time drying of thermally unstable labile mesylate under nitrogen blanket at sub zero temperatures and storage under same conditions for subsequent use in next steps.
(4) Also provides a process for pure crystalline montelukast acid.
(5) Avoids seeding during preparation of montelukast sodium salt.

The invention claimed is:

1. A process for the isolation of montelukast acid in solid form which comprises:
   (a) reacting montelukast dicyclohexylamine salt (X) with aqueous acetic acid in at least one organic solvent that is toluene or ethyl acetate;
   (b) stirring the reaction mixture of step(a);
   (c) filtering the resulting solid for recovering wet cake; and
   (d) drying the wet cake under vacuum to obtain montelukast acid in solid form having a purity of greater than or equal to 99%.

2. The process of claim 1, wherein the organic solvent used in step(a) is toluene.

3. The process of claim 1, wherein the organic solvent used in step(a) is ethyl acetate.

4. The process of claim 1, wherein the organic solvent used in step(a) is a mixture of toluene and ethyl acetate.

5. The process of claim 1, wherein montelukast acid is isolated in solid form as light yellow solid with a melting range of 148-150° C.

* * * * *